(12) United States Patent
Ober et al.

(10) Patent No.: US 8,771,917 B2
(45) Date of Patent: *Jul. 8, 2014

(54) MONOMERS, POLYMERS, PHOTORESIST COMPOSITIONS AND METHODS OF FORMING PHOTOLITHOGRAPHIC PATTERNS

(75) Inventors: Matthias S. Ober, Midland, MI (US); Young Cheol Bae, Weston, MA (US); Yi Liu, Wayland, MA (US); Seung-Hyun Lee, Marlborough, MA (US); Jong Keun Park, Hudson, MA (US)

(73) Assignees: Rohm and Haas Electronics Materials LLC, Marlborough, MA (US); Dow Global Technologies LLC, Midland, MI (US)

( * ) Notice: Subject to any disclaimer, the term of this patent is extended or adjusted under 35 U.S.C. 154(b) by 32 days.

This patent is subject to a terminal disclaimer.

(21) Appl. No.: 13/341,931

(22) Filed: Dec. 31, 2011

(65) Prior Publication Data

US 2013/0011783 A1    Jan. 10, 2013

Related U.S. Application Data

(60) Provisional application No. 61/429,101, filed on Dec. 31, 2010.

(51) Int. Cl.
*G03F 7/004* (2006.01)
*C08F 24/00* (2006.01)
*G03F 7/039* (2006.01)
*G06F 7/38* (2006.01)

(52) U.S. Cl.
CPC .............. *G03F 7/0397* (2013.01); *G06F 7/38* (2013.01); *C08F 24/00* (2013.01); *Y10S 430/111* (2013.01)
USPC ........ 430/270.1; 430/326; 430/910; 526/270; 526/329.7

(58) Field of Classification Search
CPC .......... G03F 7/0397; G03F 7/38; C08F 24/00
USPC ............. 430/270.1, 326, 910; 526/270, 329.7
See application file for complete search history.

(56) References Cited

U.S. PATENT DOCUMENTS 5,738,975 A    4/1998   Nakano et al.
(Continued)

FOREIGN PATENT DOCUMENTS

EP    1 447 403 A1    8/2004
(Continued)

OTHER PUBLICATIONS

European Search Report of corresponding European Application No. 11 19 5165.
J. Havard et al.; "Photoresists with Reduced Environmental Impact: Water Soluble Resists Based on Photo-Cross-Linking of a Sugar-Containing Polymethacrylate"; *Macromolecules* 1999, 32, pp. 86-94.
(Continued)

*Primary Examiner* — John Chu
(74) *Attorney, Agent, or Firm* — Jonathan D. Baskin

(57) ABSTRACT

Provided are (meth)acrylate monomers containing acetal moieties, polymers containing a unit formed from such a monomer and photoresist compositions containing such a polymer. The monomers, polymers and photoresist compositions are useful in forming photolithographic patterns. Also provided are substrates coated with the photoresist compositions, methods of forming photolithographic patterns and electronic devices. The compositions, methods and coated substrates find particular applicability in the manufacture of semiconductor devices.

20 Claims, 2 Drawing Sheets

(56) References Cited

U.S. PATENT DOCUMENTS

| | | | |
|---|---|---|---|
| 6,790,579 | B1 | 9/2004 | Goodall et al. |
| 2009/0176177 | A1 | 7/2009 | Han et al. |
| 2010/0330507 | A1 | 12/2010 | Tsubaki et al. |

FOREIGN PATENT DOCUMENTS

| | | | |
|---|---|---|---|
| GB | 2 097 952 A | | 11/1982 |
| JP | 61 190507 A | | 8/1986 |
| JP | 09-050126 | | 2/1997 |
| KR | 2006066932 A | | 6/2006 |
| WO | WO 90/11306 A1 | | 10/1990 |
| WO | WO 2011/105626 A1 | | 2/2011 |

OTHER PUBLICATIONS

L. Van Look et al.; "Printing the Metal and Contact Layers for the 32 and 22 nm Node: Comparing positive and negative Tone Development Process"; Proc. of SPIE, vol. 7640; 2010; pp. 764011-1-764011-12.

V. Truffert et al.; "Ultimate contact hole resolution using immersion lithography with line/space imaging"; Proc. of SPIE, vol. 7274; 2009; pp. 72740N-1-72740-12.

Koβmehl et al, "Synthesis of polymerizable xylitol derivatives", Liebigs Annalen Der Chemie, Oct. 16, 1991, pp. 1079-1081, vol. 1991, No. 10.

MONOMERS, POLYMERS, PHOTORESIST COMPOSITIONS AND METHODS OF FORMING PHOTOLITHOGRAPHIC PATTERNS

This application claims the benefit of priority under 35 U.S.C. §119(e) of U.S. Provisional Application No. 61/429,101, filed Dec. 31, 2010, the entire contents of which are incorporated herein by reference.

FIELD

The invention relates generally to the manufacture of electronic devices. More specifically, this invention relates to monomers, polymers, photoresist compositions, coated substrates and to photolithographic methods which allow for the formation of fine patterns using a negative tone development process.

BACKGROUND

In the semiconductor manufacturing industry, photoresist materials are used for transferring an image to one or more underlying layers, such as metal, semiconductor and dielectric layers, disposed on a semiconductor substrate, as well as to the substrate itself. To increase the integration density of semiconductor devices and allow for the formation of structures having dimensions in the nanometer range, photoresists and photolithography processing tools having high-resolution capabilities have been and continue to be developed.

One approach to achieving nm-scale feature sizes in semiconductor devices is the use of short wavelengths of light, for example, 193 nm or less, during exposure of chemically amplified photoresists. Immersion lithography effectively increases the numerical aperture of the lens of the imaging device, for example, a scanner having a KrF or ArF light source. This is accomplished by use of a relatively high refractive index fluid (i.e., an immersion fluid) between the last surface of the imaging device and the upper surface of the semiconductor wafer. The immersion fluid allows a greater amount of light to be focused into the resist layer than would occur with an air or inert gas medium.

The theoretical resolution limit as defined by the Rayleigh equation is shown below:

$$R = k_1 \frac{\lambda}{NA}$$

where $k_1$ is the process factor, $\lambda$ is the wavelength of the imaging tool and NA is the numerical aperture of the imaging lens. When using water as the immersion fluid, the maximum numerical aperture can be increased, for example, from 1.2 to 1.35. For a $k_1$ of 0.25 in the case of printing line and space patterns, 193 nm immersion scanners would only be capable of resolving 36 nm half-pitch line and space patterns. The resolution for printing contact holes or arbitrary 2D patterns is further limited due to the low aerial image contrast with a dark field mask wherein the theoretical limit for $k_1$ is 0.35. The smallest half-pitch of contact holes is thus limited to about 50 nm. The standard immersion lithography process is generally not suitable for manufacture of devices requiring greater resolution.

Considerable effort has been made to extend the practical resolution capabilities of positive tone development in immersion lithography from both a materials and processing standpoint. One such example involves negative tone development (NTD) of a traditionally positive-type chemically amplified photoresist. NTD is an image reversal technique allowing for use of the superior imaging quality obtained with bright field masks for printing the critical dark field layers. NTD resists typically employ a resin having acid-labile (or acid-cleavable) groups and a photoacid generator. Exposure to actinic radiation causes the photoacid generator to form an acid which, during post-exposure baking, causes cleavage of the acid-labile groups giving rise to a polarity switch in the exposed regions. As a result, a difference in solubility characteristics is created between exposed and unexposed regions of the resist such that unexposed regions of the resist can be removed by particular developers, typically organic developers such as ketones, esters or ethers, leaving behind a pattern created by the insoluble exposed regions. Such a process is described, for example, in U.S. Pat. No. 6,790,579, to Goodall et al. That document discloses a photoresist composition comprising an acid-generating initiator and a polycyclic polymer containing recurring acid labile pendant groups along the polymer backbone. The exposed areas can be selectively removed with an alkaline developer or, alternatively, the unexposed regions can be selectively removed by treatment with a suitable nonpolar solvent for negative tone development.

Certain problems can result when applying conventional 193 nm photoresists to the NTD process. The developed photoresist pattern can, for example, demonstrate significant thickness loss as compared with the pre-exposed resist layer. This can give rise to pattern defects resulting from complete erosion of portions of the resist pattern during subsequent etching. Thickness loss is believed to be caused by cleavage and loss of commonly employed bulky acid labile groups such as large tertiary alkyl ester groups from the resist layer. Thickness loss for conventional 193 nm photoresists which rely solely on such bulky acid labile groups for polarity switching can be particularly problematic due to the high content of such groups. The use of a thicker resist layer may not be a practical solution as other issues such as reduction in the depth of focus and pattern collapse can then result. The occurrence of pattern collapse when using typical 193 nm photoresists for NTD is believed to be exacerbated by the relatively high content of (meth)acrylic acid units generated in exposed regions of the photoresist following cleavage of certain acid-labile groups from (meth)acrylate-based polymers especially where such groups are solely responsible for the polarity switch. The (meth)acrylic acid units contribute to poor adhesion on organic and Si-based inorganic substrates due to the polarity mismatch between resist patterns and substrates. Another problem associated with the use in NTD of such conventional photoresists relying solely on the aforementioned bulky acid labile groups for polarity switching is etch resistance reduction.

There is a continuing need in the art for improved monomers, polymers, photoresist compositions and photolithographic methods for negative tone development which allow for the formation of fine patterns in electronic device fabrication and which avoid or conspicuously ameliorate one or more of the foregoing problems associated with the state of the art.

SUMMARY

The photoresist compositions of the invention include a polymer formed in part from a monomer which includes a particular acetal moiety. Preferred compositions and methods of the invention can result in reduced thickness loss and improvement in pattern collapse margin, resolution and photospeed in photolithographic processing.

In accordance with a first aspect of the invention, monomers are provided. The monomers are of the following general formula (I):

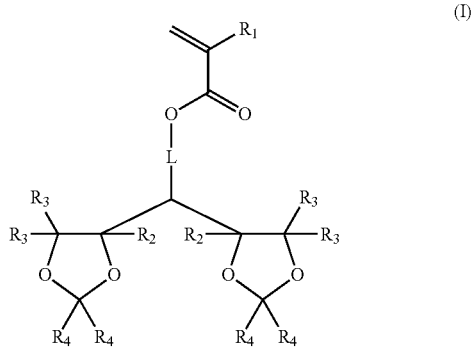

wherein: L represents a single bond or a $C_1$ to $C_{10}$ organic group; $R_1$ represents hydrogen or a $C_1$ to $C_3$ alkyl group; $R_2$ each independently represents a hydrogen atom or a $C_1$ to $C_{10}$ organic group; $R_3$ each independently represents a hydrogen atom or a $C_1$ to $C_{10}$ organic group, those bonded to a common carbon atom together optionally forming a ring; and $R_4$ each independently represents a $C_1$ to $C_{10}$ organic group, those bonded to a common carbon atom together optionally forming a ring.

In accordance with a further aspect of the invention, provided are methods of preparing monomers of general formula (I) as described above.

In accordance with a further aspect of the invention, polymers are provided. The polymers comprise a unit formed from a monomer of general formula (I) as described above. The polymers can take the form of a homopolymer or a copolymer containing one, two, three, four or more additional units. For example, the polymer preferably further comprises a second unit comprising a lactone moiety and a third unit comprising an ether, an ester, a polar group or an acid labile moiety, wherein the third unit is different from the first unit and the second unit.

In accordance with a further aspect of the invention, photoresist compositions are provided. The photoresist compositions comprise a polymer of the invention as described herein and a photoacid generator.

Also provided are methods of forming photolithographic patterns. The methods comprise: (a) providing a substrate comprising one or more layer to be patterned over a surface of the substrate; (b) applying a layer of a photoresist composition of the invention as described herein over the one or more layer to be patterned; (c) patternwise exposing the photoresist composition layer to actinic radiation; (d) heating the exposed photoresist composition layer in a post-exposure bake process; and (e) applying a developer to the photoresist composition layer to remove a portion of the photoresist layer, thereby forming a photoresist pattern. In a negative tone development method, unexposed regions of the photoresist layer are removed by the developer to form the photoresist pattern. In a positive tone development method, exposed regions of the photoresist layer are removed by the developer to form the photoresist pattern.

Also provided are coated substrates. The coated substrates comprise a substrate and a layer of a photoresist composition of the invention as described herein over a surface of the substrate.

Also provided are electronic devices formed by the methods described herein.

As used herein: "g" means grams; wt % means weight percent; "L" means liter; "mL" means milliliter; "nm" means nanometer; "mm" means millimeter; "min" means minute; "h" means hour; "Å" means Angstroms; "mol %" means mole percent; "Mw" means weight average molecular weight; and "Mn" means number average molecular weight; the articles "a" and "an" mean one or more.

BRIEF DESCRIPTION OF THE DRAWINGS

The present invention will be described with reference to the following drawings, in which like reference numerals denote like features, and in which.

DETAILED DESCRIPTION

Monomers

Figure 1A:
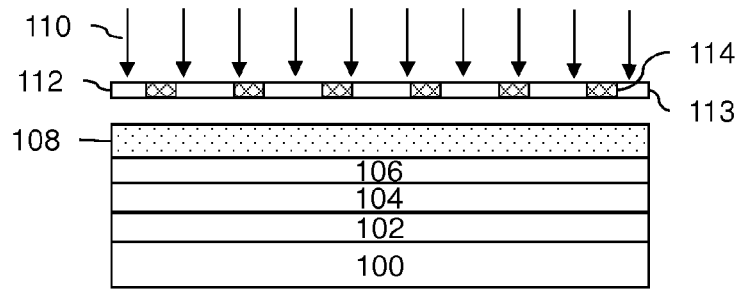
FIG. 1A-E illustrates a process flow for forming a photolithographic pattern in accordance with the invention.

The monomers of the invention include a plurality of ring structures, each having and an acetal group. As used herein, the terms acetal and acetal group(s) are inclusive of ketal and ketal group(s), respectively. The two oxygen atoms and secondary carbon atom ("acetal secondary carbon atom") bonded to the oxygen atoms in each ring, characteristic of the acetal group, form a portion of the ring structure. Bonded to the acetal secondary carbon atom is a structure which can, for example, take the form of two groups pendant to the ring structure or which together with the acetal secondary carbon atom can take the form of a ring structure. The acetal secondary carbon atom together with the pendant group(s) are acid labile, capable of undergoing a photoacid-promoted deprotection reaction on exposure to activating radiation and heat treatment. The resulting cleavage of the acetal secondary carbon atom and pendant group(s) of the rings is believed to result in the formation of hydroxy groups with the former acetal oxygen atoms. This is believed to cause the monomer to become less soluble or substantially insoluble in an organic solvent. As a result, polymers formed from the monomers and photoresist compositions containing such polymers can be made which become less soluble or substantially insoluble in an organic solvent, allowing for the formation of a negative-type image in a layer of such a photoresist composition.

The monomers are of the following general formula (I):

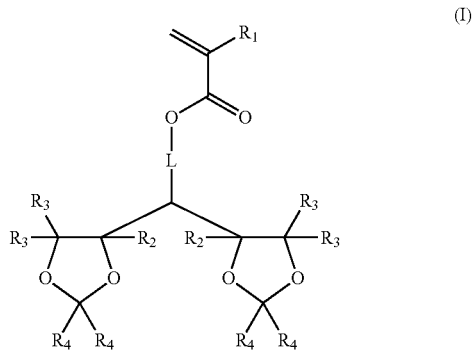

In formula (I), L represents a single bond or a $C_1$ to $C_{10}$ organic group, for example, $C_1$ to $C_{10}$ or $C_1$ to $C_6$ alkylene, $C_2$ to $C_{10}$ or $C_2$ to $C_6$ alkenylene, $C_3$ to $C_8$ alicyclic, a $C_2$ to $C_{10}$ or $C_2$ to $C_7$ alkyl ester, or a $C_2$ to $C_{10}$ or $C_2$ to $C_8$ alkyl ether. $R_1$ represents hydrogen or a $C_1$ to $C_3$ alkyl group, typically hydrogen or methyl. $R_2$ independently represents a hydrogen atom or a $C_1$ to $C_{10}$ organic group such as $C_1$ to $C_{10}$ or $C_1$ to $C_6$ alkyl, $C_2$ to $C_{10}$ or $C_2$ to $C_6$ alkenyl. Each $R_3$ independently represents a hydrogen atom or a $C_1$ to $C_{10}$ organic group, for example, $C_1$ to $C_{10}$ or $C_1$ to $C_6$ alkyl, aldehyde, alkoxycarbonyl, benzyloxymethyl, phenylsulfonyloxymethyl or tosyloxymethyl. Those $R_3$ groups bonded to a common carbon atom together can optionally form a ring. Each $R_4$ independently represents a $C_1$ to $C_{10}$ organic group such as a $C_1$ to $C_{10}$ or $C_1$ to $C_6$ alkyl or acetyloxy group, and together optionally form a ring such as a $C_3$ to $C_6$ or $C_4$ to $C_6$ cycloalkyl ring. It shall be understood for purposes of the description and claims that the various R groups as defined herein can optionally be substituted, meaning that one or more hydrogen atom can be replaced by another atom such as a halogen, for example, fluorine. The content of the first unit in the polymer, while dependent on the number and types of different units making up the polymer, is typically from 30 to 60 mol %.

Typically, the monomer has the following general structure:

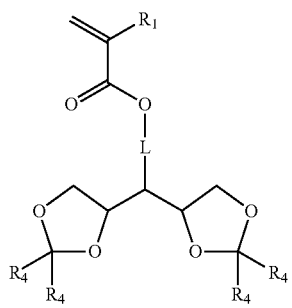

wherein $R_1$ and $R_4$ are as described above with reference to formula (I).

Without limitation, suitable monomers of formula (I) include, for example, the following:

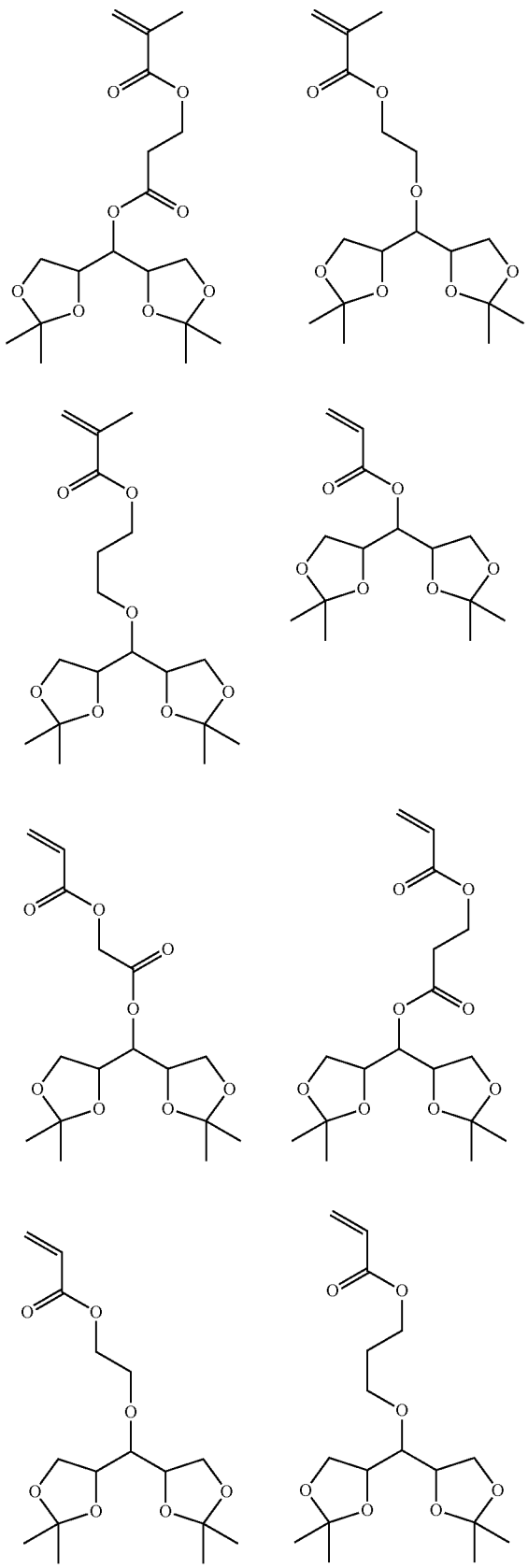

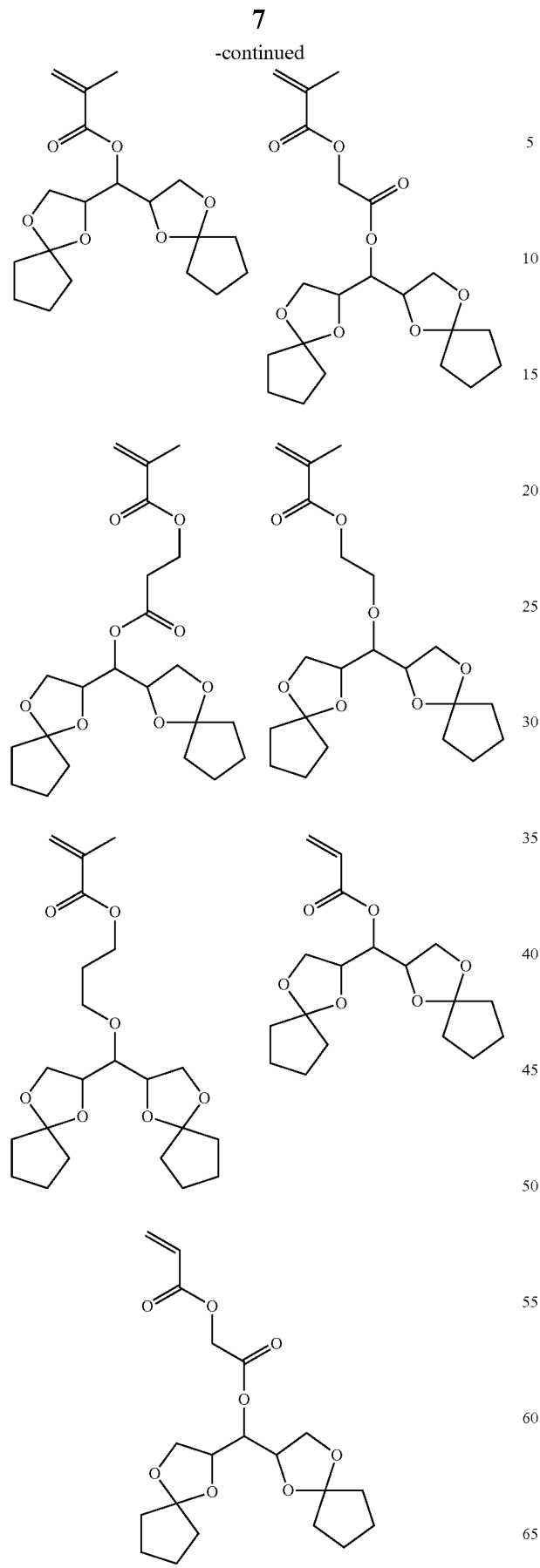
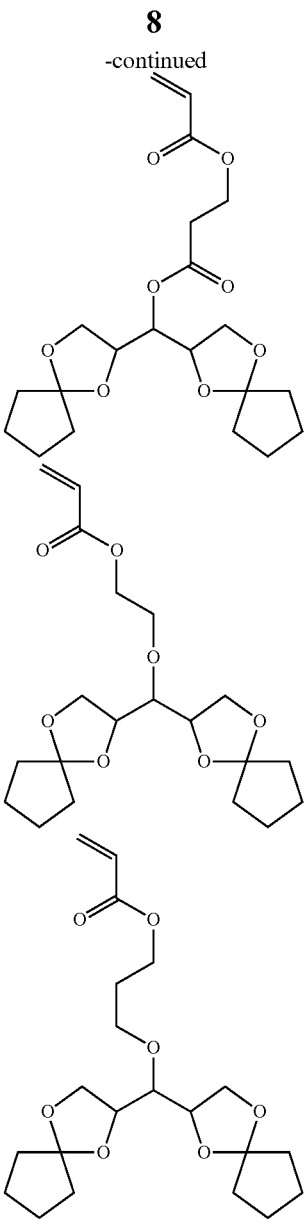

Of these, bis(2,2-dimethyl-1,3-dioxolan-4-yl)methyl methacrylate (IPRMA) is preferred. Monomers of formula (I) can be synthesized using known techniques, for example, subjecting the corresponding polyalcohol, in which two hydroxyl group pairs are individually joined together in a pair of acetal groups, to esterification with acryloyl chloride, methacryloyl chloride, ethacryloyl chloride or propacryloyl chloride. Additional suitable synthesis techniques are described in U.S. Pat. No. 7,416,867B2 and involve subjecting the corresponding polyalcohol, in which two hydroxyl groups are joined in an acetal group, to esterification with (alkyl)acrylic acid or to transesterification with an (alkyl)acrylic ester in the presence of an enzyme. Techniques for forming acetal groups in a protection reaction with the corresponding alcohol can be carried out, for example, as described by Levene and Tipson, J. Biological Chem, 1936 p 731, Orgmikum, VEB Deutscher Verlag der Wissenschaften, 17th edition, Berlin 1988, p. 398 or Protective Groups in Organic Synthesis, Wuts and Greene, Wiley-Interscience; 4th Edition, Oct. 30, 2006.

A particularly preferred method in accordance with the invention for preparation of monomers of general formula (I)

is described below in the Examples, with bis(2,2-dimethyl-1,3-dioxolan-4-yl)methyl methacrylate monomer being exemplified. This technique involves a three step reaction using a special separation step of intermediate isomers. 1,2:4,5-diisopropylideneribitol can be effectively separated to make pure (isomer free) 1,2:4,5-diisopropylideneribitol-based polymerizable monomers allowing for the preparation of pure bis(2,2-dimethyl-1,3-dioxolan-4-yl)methyl methacrylate monomer.

Polymers

The polymers of the invention include a first unit formed from a monomer of formula (I) as described above. The polymer can take the form of a homopolymer including a unit formed from a monomer of formula (I). Optionally, the polymer can include one or more additional units, for example, one two, three, four or more additional units different from the first unit. The polymer can, for example, include one or more additional unit formed from monomers of formula (I) different from the first unit and/or from other monomers. Typically, the additional units will include the same (meth)acrylate polymerizable group as that used for the monomers of the first unit but can include different polymerizable groups. While the content of the first unit will depend on the number and type of different units making up the polymer, it is typically present in the polymer in an amount of from 30 to 60 mol %.

The polymer preferably further includes a second unit formed from a monomer comprising a lactone moiety. The second unit is typically present in the polymer in an amount of from 20 to 60 mol %. Suitable such lactone moieties are known in the art and include, for example, those of the following formulae:

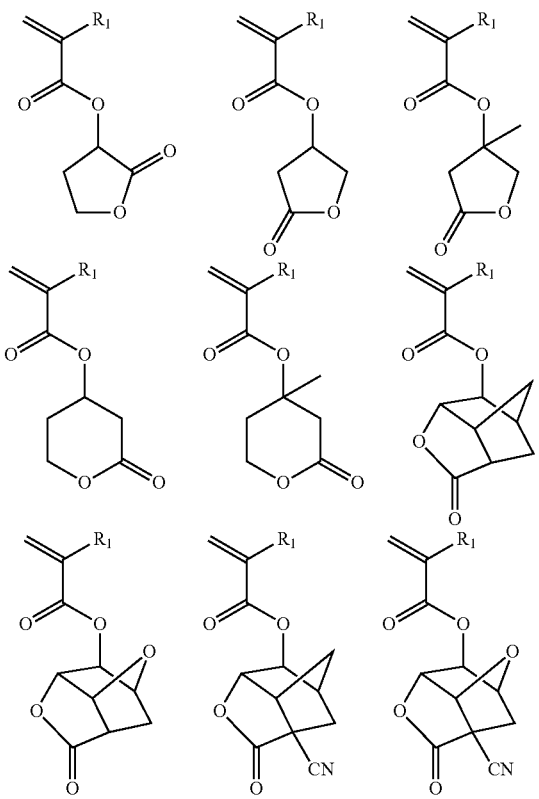

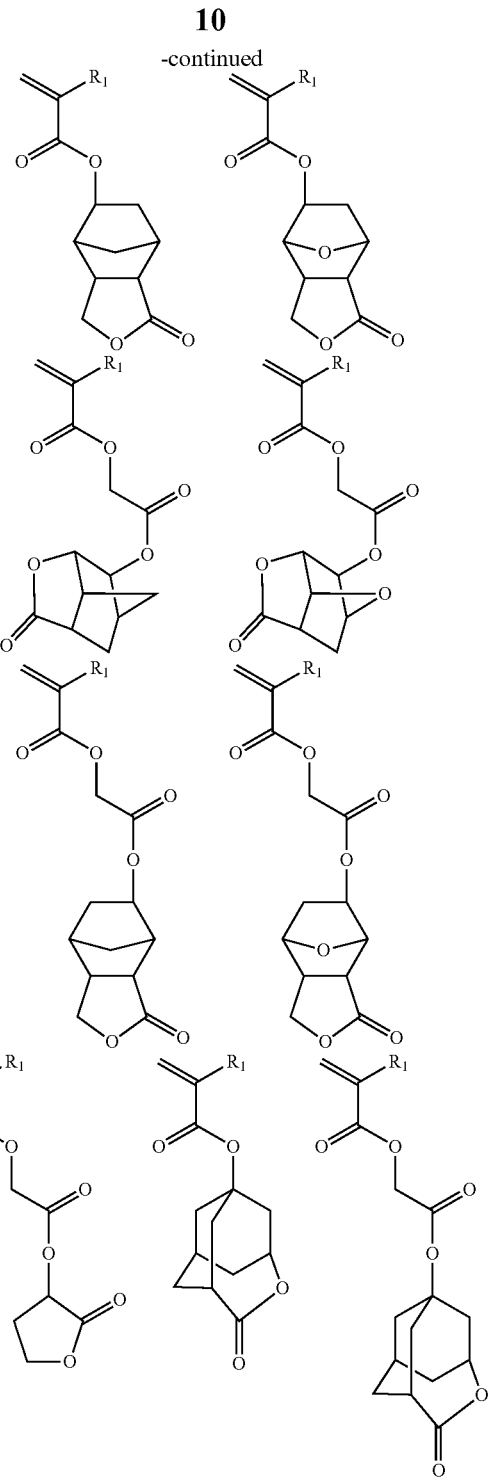

wherein $R_1$ is as defined above as being chosen from hydrogen and C1 to C3 alkyl, preferably hydrogen or methyl. Suitable monomers for the second unit are commercially available and/or can be synthesized using known techniques.

Other suitable additional monomeric units for the polymer include, for example, one or more of the following: monomeric units formed from a monomer comprising a moiety of formula (I) which is different from the first unit; monomeric units containing ethers, lactones or esters, such as 2-methyl-acrylic acid tetrahydro-furan-3-yl ester, 2-methyl-acrylic acid 2-oxo-tetrahydro-furan-3-yl ester, 2-methyl-acrylic acid 5-oxo-tetrahydro-furan-3-yl ester, 2-methyl-acrylic acid 3-oxo-4,10-dioxa-tricyclo[5.2.1.02,6]dec-8-yl ester, 2-methyl-acrylic acid 3-oxo-4-oxa-tricyclo[5.2.1.02,6]dec-8-yl ester, 2-methyl-acrylic acid 5-oxo-4-oxa-tricyclo[4.2.1.03,7]non-2-yloxycarbonylmethyl ester, acrylic acid 3-oxo-4-oxa-tricyclo[5.2.1.02,6]dec-8-yl ester, 2-methyl-acrylic acid 5-oxo-4-oxa-tricyclo[4.2.1.03,7]non-2-yl ester, and 2-methyl-acrylic acid tetrahydro-furan-3-yl ester; monomeric units having polar groups such as alcohols and fluorinated alcohols, such as 2-methyl-acrylic acid 3-hydroxy-adamantan-1-yl ester, 2-methyl-acrylic acid 2-hydroxy-ethyl ester, 6-vinyl-naphthalen-2-ol, 2-methyl-acrylic acid 3,5-dihydroxy-adamantan-1-yl ester, 2-methyl-acrylic acid 6-(3,3,3-trifluoro-2-hydroxy-2-trifluoromethyl-propyl)-bicyclo[2.2.1]hept-2-yl, and 2-bicyclo[2.2.1]hept-5-en-2-ylmethyl-1,1,1,3,3,3-hexafluoro-propan-2-ol; monomeric units having acid labile moieties, for example, ester groups that contain a tertiary non-cyclic alkyl carbon such as t-butyl, or a tertiary alicyclic carbon such as methyladamantyl or ethylfenchyl covalently linked to a carboxyloxygen of an ester of the polymer, 2-methyl-acrylic acid 2-(1-ethoxy-ethoxy)-ethyl ester, 2-methyl-acrylic acid 2-ethoxymethoxy-ethyl ester, 2-methyl-acrylic acid 2-methoxymethoxy-ethyl ester, 2-(1-ethoxy-ethoxy)-6-vinyl-naphthalene, 2-ethoxymethoxy-6-vinyl-naphthalene, and 2-methoxymethoxy-6-vinyl-naphthalene. Suitable monomers for such additional units are commercially available and/or can be synthesized using known methods. The additional units are typically present in the polymer in an amount of from 40 to 70 mol %.

For imaging at sub-200 nm wavelengths such as 193 nm, the polymer is typically substantially free (e.g., less than 15 mol %) of phenyl, benzyl or other aromatic groups where such groups are highly absorbing of the radiation. The polymer can contain repeat units that contain a hetero atom, particularly oxygen and/or sulfur, for example, one or more chosen from: heteroalicyclic units fused to the polymer backbone; fused carbon alicyclic units such as provided by polymerization of a norbornene group; and carbocyclic aryl units substituted with one or more hetero-atom-containing (e.g., oxygen or sulfur) groups, for example, hydroxy naphthyl groups.

Preferred polymers in accordance with the invention include, for example, the following:

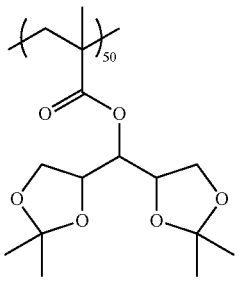
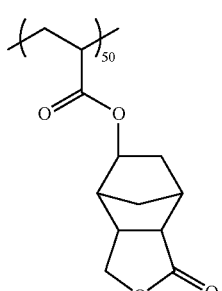
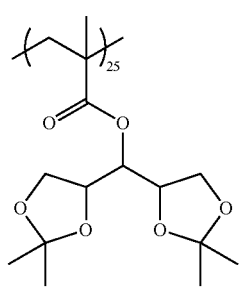
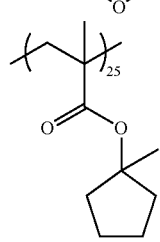

-continued

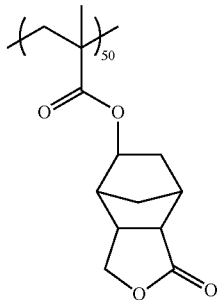
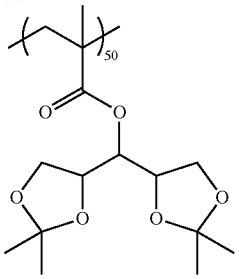
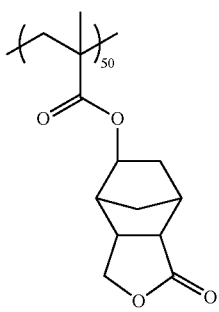
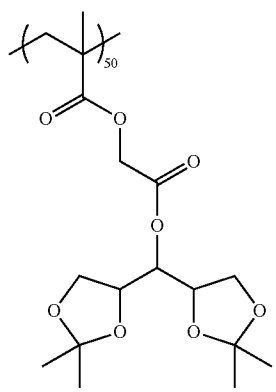
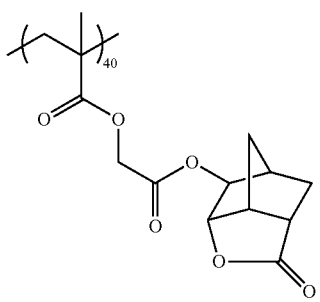
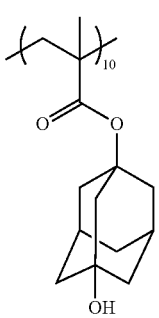
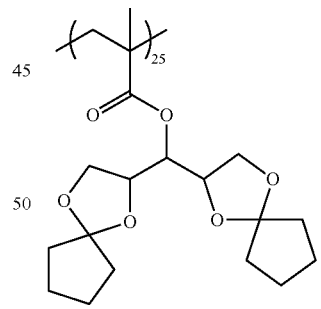
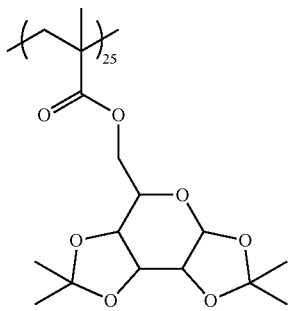
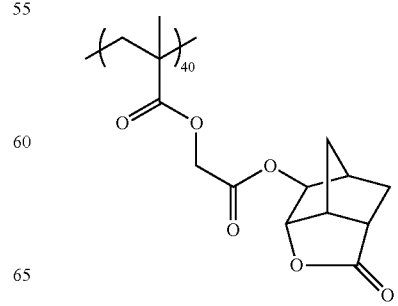
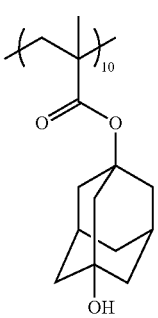

-continued

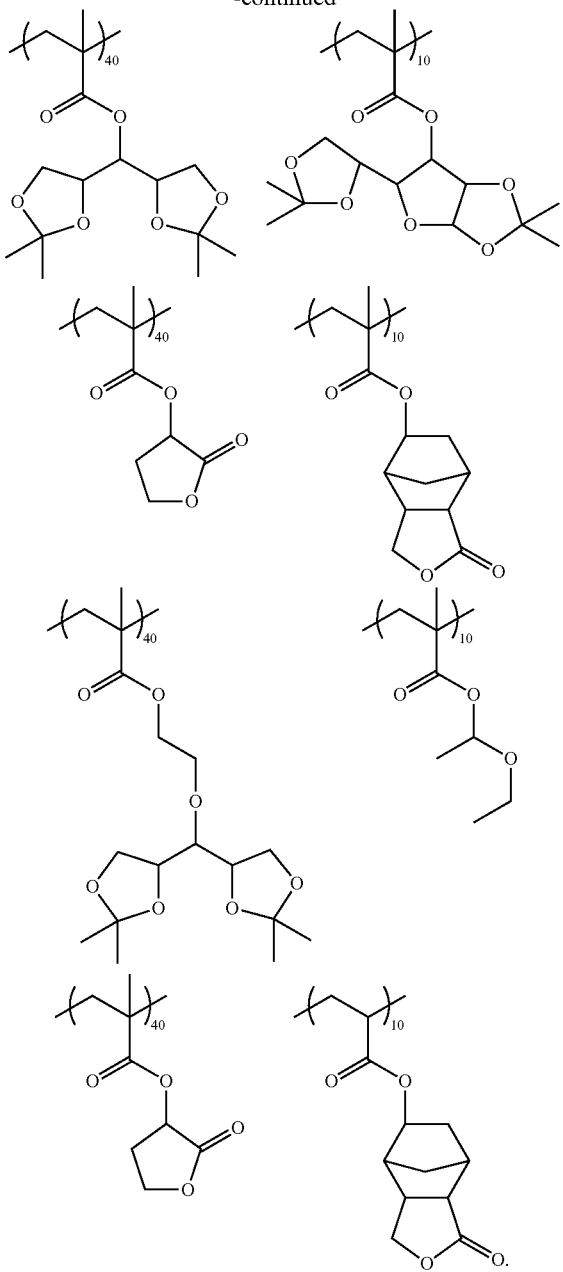

The weight average molecular weight $M_w$ of the polymers of the invention is typically less than 100,000, for example, from 5000 to 50,000, more typically from 7000 to 30,000 or from 10,000 to 25,000.

Suitable polymers in accordance with the invention can readily be synthesized by persons skilled in the art using known methods and commercially available starting materials. The polymers can be synthesized, for example, by first dissolving the polymerizable group-containing monomers in a suitable organic solvent, for example, tetrahydrofuran, dioxane, ethyl acetate, dimethyl formamide, propylene glycol methyl ether acetate (PGMEA), methylene chloride, chloroform, acetone, methyl ethyl ketone or the like, and degassing. A radical initiator can be dissolved in a suitable solvent which is the same or different from that used for the monomer dissolution, and then added to the monomer solution. Suitable radical initiators include, for example, 2,2'-azobisisobutyronitrile (AIBN), dimethyl 2,2'-azobis(2-methylpropionate) (Vazo™601, DuPont), 2,2'-azobis(2,4-dimethyl)valeronitrile (Vazo™52, DuPont) and 2,2-azobis(2-methylbutane-nitrile) (Vazo™67, DuPont). A reaction vessel is charged with a solvent which is the same or different from that used for the monomer solution and is heated to a temperature of from 40 to 140° C., typically from 70 to 80° C. The initiator solution can then be added to the reaction vessel, and the monomer solution added in a drop-wise manner to the vessel. The reaction mixture can be cooled and slowly added to a rapidly stirred non-solvent for precipitation. Suitable non-solvents include, for example, water, alcohols, alkanes, ethers, and combinations thereof. The polymer is collected, optionally rinsed with a small amount of non-solvent and dried. For further purification, the polymer can be re-dissolved in a suitable solvent, precipitated and dried.

Photoresist Compositions

Preferred photoresist compositions of the invention when used to form very fine patterns in a negative tone development process can provide improvements in one or more of resolution, top loss, pattern collapse, focus latitude, exposure latitude, photospeed and defectivity as compared with conventional positive-tone photolithographic techniques. Preferred photoresists can further provide geometrically uniform resist patterns for lines and contact holes. The compositions described herein can be used in dry lithography or immersion lithography processes. The photoresist compositions also find use in positive tone development processes.

A. Matrix Polymer

The photoresist compositions include a matrix polymer such as the polymers described above. The matrix polymer as part of a layer of the photoresist composition undergoes a change in solubility in an organic developer as a result of reaction with acid generated from the photoacid generator following softbake, exposure to activating radiation and post exposure bake.

The matrix polymer is present in the resist composition in an amount sufficient to obtain a uniform coating of desired thickness. Typically, the matrix polymer is present in the composition in an amount of from 70 to 95 wt % based on total solids of the resist composition.

B. Photoacid Generator

The photosensitive composition further comprises a photoacid generator (PAG) employed in an amount sufficient to generate a latent image in a coating layer of the composition upon exposure to activating radiation. For example, the photoacid generator will suitably be present in an amount of from about 1 to 20 wt % based on total solids of the photoresist composition. Typically, lesser amounts of the PAG will be suitable for chemically amplified resists as compared with non-chemically amplified materials.

Suitable PAGs are known in the art of chemically amplified photoresists and include, for example: onium salts, for example, triphenylsulfonium trifluoromethanesulfonate, (p-tert-butoxyphenyl)diphenylsulfonium trifluoromethanesulfonate, tris(p-tert-butoxyphenyl)sulfonium trifluoromethanesulfonate, triphenylsulfonium p-toluenesulfonate; nitrobenzyl derivatives, for example, 2-nitrobenzyl-p-toluenesulfonate, 2,6-dinitrobenzyl-p-toluenesulfonate, and 2,4-dinitrobenzyl-p-toluenesulfonate; sulfonic acid esters, for example, 1,2,3-tris(methanesulfonyloxy)benzene, 1,2,3-tris (trifluoromethanesulfonyloxy)benzene, and 1,2,3-tris(p-toluenesulfonyloxy)benzene; diazomethane derivatives, for example, bis(benzenesulfonyl)diazomethane, bis(p-toluenesulfonyl)diazomethane; glyoxime derivatives, for example, bis-O-(p-toluenesulfonye-α-dimethylglyoxime, and bis-O-(n-butanesulfonyl)-α-dimethylglyoxime; sulfonic acid ester derivatives of an N-hydroxyimide compound, for example, N-hydroxysuccinimide methanesulfonic acid ester, N-hydroxysuccinimide trifluoromethanesulfonic acid ester; and halogen-containing triazine compounds, for example, 2-(4-methoxyphenyl)-4,6-bis(trichloromethyl)-1,3,5-triazine, and 2-(4-methoxynaphthyl)-4,6-bis(trichloromethyl)-1,3,5-triazine. One or more of such PAGs can be used.

C. Solvent

Suitable solvents for the photoresist compositions of the invention include, for example: glycol ethers such as 2-methoxyethyl ether (diglyme), ethylene glycol monomethyl ether, and propylene glycol monomethyl ether; propylene glycol monomethyl ether acetate; lactates such as methyl lactate and ethyl lactate; propionates such as methyl propionate, ethyl propionate, ethyl ethoxy propionate and methyl-2-hydroxy isobutyrate; Cellosolve esters such as methyl Cellosolve acetate; aromatic hydrocarbons such as toluene and xylene; and ketones such as acetone, methylethyl ketone, cyclohexanone and 2-heptanone. A blend of solvents such as a blend of two, three or more of the solvents described above also are suitable. The solvent is typically present in the composition in an amount of from 90 to 99 wt %, more typically from 95 to 98 wt %, based on the total weight of the photoresist composition.

D. Other Components

The photoresist compositions can also include other optional materials. For example, the compositions can include one or more of actinic and contrast dyes, anti-striation agents, plasticizers, speed enhancers, sensitizers, and the like. Such optional additives if used are typically present in the composition in minor amounts such as from 0.1 to 10 wt % based on total solids of the photoresist composition.

A preferred optional additive of resist compositions of the invention is an added base, for example, a caprolactam, which can enhance resolution of a developed resist relief image. Other suitable basic additives include: alkyl amines such as tripropylamine and dodecylamine, aryl amines such as diphenylamine, triphenylamine, aminophenol, 2-(4-aminophenyl)-2-(4-hydroxyphenyl)propane, and the like. The added base is suitably used in relatively small amounts, for example, from 0.01 to 5 wt %, preferably from 0.1 to 2 wt %, based on total solids of the photoresist composition.

Surface active polymers can optionally be used as an additive in the photoresist formulation in order to simplify the immersion lithographic process by avoiding the need for a top-coat layer over the resist layer. Top-coat layers are typically used to prevent resist components such as photoacid generators from contaminating the imaging lens surface. Surface active polymer additives added to the photoresist formulations migrate to the surface during the coating process due to their relatively low surface free energy. The surface active polymer additives should have a lower surface free energy than the matrix polymer to allow the surface active polymer to migrate to the surface. A typical surface free energy of the surface active polymer additives is from 10 to 40 mJ/m$^2$. Suitable surface active polymers are known in the art and include, for example, those disclosed by Tsibouklis and Nevell (Advanced Materials, 2003, 15, pp. 647-650). Exemplary suitable polymer additives include, for example, poly(n-butyl acrylate), poly(n-butyl methacrylate), poly(1-butyl acrylate), poly(1-butyl methacrylate), poly(diethyl siloxane), poly(vinyl butyrate), polytetrahydrofuran, poly(propylene glycol), poly(tetramethylene oxide) and fluorinated polymers. The one or more additive polymer typically may be present in the photoresist composition in relatively small amounts and still provide effective results. The content of the additive polymer may depend, for example, on whether the lithography is a dry or immersion-type process. For example, the additive polymer lower limit for immersion lithography is generally dictated by the need to prevent leaching of the resist components. A higher additive polymer content will typically result in pattern degradation. The one or more polymer additive is typically present in the compositions of the invention in an amount of from 0.1 to 10 wt %, more typically from 1 to 5 wt %, based on total solids of the photoresist composition. The weight average molecular weight of the additive polymer is typically less than 400,000, for example from 5000 to 50,000.

Preparation of Photoresist Compositions

The photoresists used in accordance with the invention are generally prepared following known procedures. For example, a photoresist composition of the invention can be prepared by dissolving the components of the photoresist in the solvent component. The desired total solids content of the photoresist will depend on factors such as the particular polymers in the composition, final layer thickness and exposure wavelength. Typically the solids content of the photoresist varies from 1 to 10 wt %, more typically from 2 to 5 wt %, based on the total weight of the photoresist composition.

Photoresist compositions of the invention find particular applicability in negative-tone development processes such as described below, but can be used in positive-tone development wherein exposed portions of the photoresist layer are removed in developer solutions.

Negative Tone Development Methods

The invention further provides methods for forming a photoresist relief image and producing an electronic device using photoresists of the invention. The invention also provides novel articles of manufacture comprising substrates coated with a photoresist composition of the invention. Processes in accordance with the invention will now be described with reference to FIG. 1A-E, which illustrates an exemplary process flow for forming a photolithographic pattern by negative tone development.

FIG. 1A depicts in cross-section a substrate 100 which may include various layers and features. The substrate can be of a material such as a semiconductor, such as silicon or a compound semiconductor (e.g., III-V or II-VI), glass, quartz, ceramic, copper and the like. Typically, the substrate is a semiconductor wafer, such as single crystal silicon or compound semiconductor wafer, and may have one or more layers and patterned features formed on a surface thereof. One or more layers to be patterned 102 may be provided over the substrate 100. Optionally, the underlying base substrate material itself may be patterned, for example, when it is desired to form trenches in the substrate material. In the case of patterning the base substrate material itself, the pattern shall be considered to be formed in a layer of the substrate.

The layers may include, for example, one or more conductive layers such as layers of aluminum, copper, molybdenum, tantalum, titanium, tungsten, alloys, nitrides or silicides of such metals, doped amorphous silicon or doped polysilicon, one or more dielectric layers such as layers of silicon oxide, silicon nitride, silicon oxynitride, or metal oxides, semiconductor layers, such as single-crystal silicon, and combinations thereof. The layers to be etched can be formed by various techniques, for example, chemical vapor deposition (CVD) such as plasma-enhanced CVD, low-pressure CVD or epitaxial growth, physical vapor deposition (PVD) such as sputtering or evaporation, or electroplating. The particular thickness of the one or more layers to be patterned 102 will vary depending on the materials and particular devices being formed.

Depending on the particular layers to be etched, film thicknesses and photolithographic materials and process to be used, it may be desired to dispose over the layers 102a hard mask layer 104 and/or a bottom antireflective coating (BARC) 106 over which a photoresist layer 108 is to be coated. Use of a hard mask layer 104 may be desired, for example, with very thin resist layers, where the layers to be etched require a significant etching depth, and/or where the particular etchant has poor resist selectivity. Where a hard mask layer is used, the resist patterns to be formed can be transferred to the hard mask layer which, in turn, can be used as a mask for etching the underlying layers 102. Suitable hard mask materials and formation methods are known in the art. Typical materials include, for example, tungsten, titanium, titanium nitride, titanium oxide, zirconium oxide, aluminum oxide, aluminum oxynitride, hafnium oxide, amorphous carbon, silicon oxynitride and silicon nitride. The hard mask layer 104 can include a single layer or a plurality of layers of different materials. The hard mask layer can be formed, for example, by chemical or physical vapor deposition techniques.

A bottom antireflective coating 106 may be desirable where the substrate and/or underlying layers would otherwise reflect a significant amount of incident radiation during photoresist exposure such that the quality of the formed pattern would be adversely affected. Such coatings can improve depth-of-focus, exposure latitude, linewidth uniformity and CD control. Antireflective coatings are typically used where the resist is exposed to deep ultraviolet light (300 nm or less), for example, KrF excimer laser light (248 nm) or ArF excimer laser light (193 nm). The antireflective coating 106 can comprise a single layer or a plurality of different layers. Suitable antireflective materials and methods of formation are known in the art. Antireflective materials are commercially available, for example, those sold under the AR™ trademark by Rohm and Haas Electronic Materials LLC (Marlborough, Mass. USA), such as AR™40A and AR™124 antireflectant materials.

A photoresist composition as described herein is applied on the substrate over the antireflective layer 106 (if present) to form a photoresist layer 108. The photoresist composition can be applied to the substrate by spin-coating, dipping, roller-coating or other conventional coating technique. Of these, spin-coating is typical. For spin-coating, the solids content of the coating solution can be adjusted to provide a desired film thickness based upon the specific coating equipment utilized, the viscosity of the solution, the speed of the coating tool and the amount of time allowed for spinning. A typical thickness for the photoresist layer 108 is from about 500 to 3000 Å.

The photoresist layer can next be softbaked to minimize the solvent content in the layer, thereby forming a tack-free coating and improving adhesion of the layer to the substrate. The softbake can be conducted on a hotplate or in an oven, with a hotplate being typical. The softbake temperature and time will depend, for example, on the particular material of the photoresist and thickness. Typical softbakes are conducted at a temperature of from about 90 to 150° C., and a time of from about 30 to 90 seconds.

The photoresist layer 108 is next exposed to activating radiation 110 through a first photomask 112 to create a difference in solubility between exposed and unexposed regions. References herein to exposing a photoresist composition to radiation that is activating for the composition indicates that the radiation is capable of forming a latent image in the photoresist composition. The photomask has optically transparent and optically opaque regions 113, 114 corresponding to regions of the resist layer to remain and be removed, respectively, in a subsequent development step for a positive-acting material as illustrated. The exposure wavelength is typically sub-400 nm, sub-300 nm or sub-200 nm, with 248 nm and 193 nm being typical. The methods find use in immersion or dry (non-immersion) lithography techniques. The exposure energy is typically from about 10 to 80 mJ/cm$^2$, dependent upon the exposure tool and the components of the photosensitive composition.

Figure 1B:
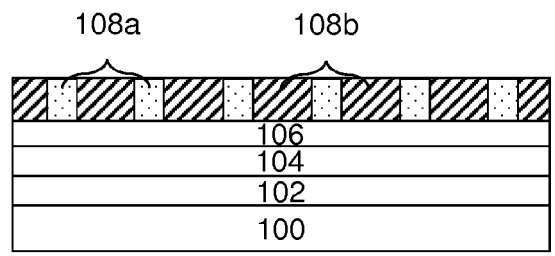

As shown in FIG. 1B, the exposed resist layer is made up of unexposed and exposed regions 108a, 108b. Following exposure of the photoresist layer 108, a post-exposure bake (PEB) is performed. The PEB can be conducted, for example, on a hotplate or in an oven. Conditions for the PEB will depend, for example, on the particular photoresist composition and layer thickness. The PEB is typically conducted at a temperature of from about 80 to 150° C., and a time of from about 30 to 90 seconds.

Figure 1C:
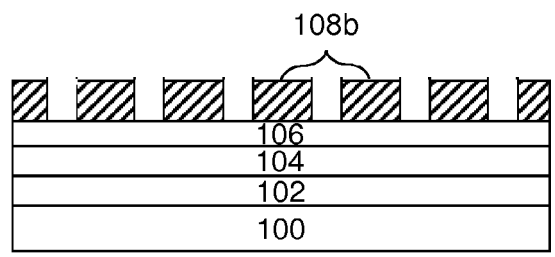

The exposed photoresist layer is next developed to remove unexposed regions 108a, leaving exposed regions 108b forming a resist pattern as shown in FIG. 1C. The developer is typically an organic developer, for example, a solvent chosen from ketones, esters, ethers, hydrocarbons, and mixtures thereof. Suitable ketone solvents include, for example, acetone, 2-hexanone, 5-methyl-2-hexanone, 2-heptanone, 4-heptanone, 1-octanone, 2-octanone, 1-nonanone, 2-nonanone, diisobutyl ketone, cyclohexanone, methylcyclohexanone, phenylacetone, methyl ethyl ketone and methyl isobutyl ketone. Suitable ester solvents include, for example, methyl acetate, butyl acetate, ethyl acetate, isopropyl acetate, amyl acetate, propylene glycol monomethyl ether acetate, ethylene glycol monoethyl ether acetate, diethylene glycol monobutyl ether acetate, diethylene glycol monoethyl ether acetate, ethyl-3-ethoxypropionate, 3-methoxybutyl acetate, 3-methyl-3-methoxybutyl acetate, methyl formate, ethyl formate, butyl formate, propyl formate, ethyl lactate, butyl lactate and propyl lactate. Suitable ether solvents include, for example, dioxane, tetrahydrofuran and glycol ether solvents, for example, ethylene glycol monomethyl ether, propylene glycol monomethyl ether, ethylene glycol monoethyl ether, propylene glycol monoethyl ether, diethylene glycol monomethyl ether, triethylene glycol monoethyl ether and methoxymethyl butanol. Suitable amide solvents include, for example, N-methyl-2-pyrrolidone, N,N-dimethylacetamide and N,N-dimethylformamide. Suitable hydrocarbon solvents include, for example, aromatic hydrocarbon solvents such as toluene and xylene. In addition, mixtures of these solvents, or one or more of the listed solvents mixed with a solvent other than those described above or mixed with water can be used. Of these, 2-heptanone and 5-methyl-2-hexanone are particularly preferred. Other suitable solvents include those used in the photoresist composition.

The solvent can be present in the developer as a substantially pure material, for example, in an amount greater than 95 wt %, greater than 98 wt % or greater than 99 wt %, based on the total weight of the developer. In the case a mixture of solvents are used in the developer, the boiling points of the solvents are preferably similar. The solvents of the developer are typically present in an amount of from 50 wt % to 100 wt %, more typically from 80 wt % to 100 wt %, based on the total weight of the developer.

The developer material may include optional additives, for example, surfactants such as described above with respect to the photoresist. Such optional additives typically will be present in minor concentrations, for example, in amounts of from about 0.01 to 5 wt % based on the total weight of the developer.

The developer can be applied to the substrate by known techniques, for example, by spin-coating or puddle-coating. The development time is for a period effective to remove the unexposed regions of the photoresist, with a time of from 5 to 30 seconds being typical. Development is typically conducted at room temperature. The development process can be conducted without use of a cleaning rinse following development. In this regard, it has been found that the development process can result in a residue-free wafer surface rendering such extra rinse step unnecessary.

Figure 1D:
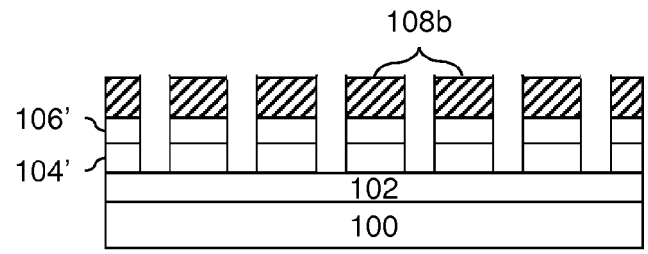

The BARC layer 106, if present, is selectively etched using resist pattern 108b as an etch mask, exposing the underlying hardmask layer 104. The hardmask layer is next selectively etched, again using the resist pattern 108b as an etch mask, resulting in patterned BARC and hardmask layers 106', 104', as shown in FIG. 1D. Suitable etching techniques and chemistries for etching the BARC layer and hardmask layer are known in the art and will depend, for example, on the particular materials of these layers. Dry-etching processes such as reactive ion etching are typical. The resist pattern 108b and patterned BARC layer 106' are next removed from the substrate using known techniques, for example, oxygen plasma ashing.

Figure 1E:
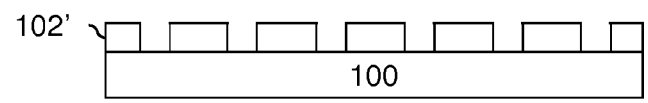

Using the hardmask pattern 104' as an etch mask, the one or more layers 102 are selectively etched. Suitable etching techniques and chemistries for etching the underlying layers 102 are known in the art, with dry-etching processes such as reactive ion etching being typical. The patterned hardmask layer 104' can next be removed from the substrate surface using known techniques, for example, a dry-etching process such as reactive ion etching. The resulting structure is a pattern of etched features 102' as illustrated in FIG. 1E. In an alternative exemplary method, it may be desirable to pattern the layer 102 directly using the resist pattern 108b without the use of a hardmask layer 104. Whether direct patterning is employed will depend on factors such as the materials involved, resist selectivity, resist pattern thickness and pattern dimensions.

The negative tone development methods of the invention are not limited to the exemplary methods described above. For example, the photoresist compositions of the invention can be used in a negative tone development double exposure method for making contact holes. An exemplary such process is a variation of the technique described with reference to FIG. 1, but using an additional exposure of the photoresist layer in a different pattern than the first exposure. In this process, the photoresist layer is exposed to actinic radiation through a photomask in a first exposure step. The photomask includes a series of parallel lines forming the opaque regions of the mask. Following the first exposure, a second exposure of the photoresist layer is conducted through a second photomask that includes a series of lines in a direction perpendicular to those of the first photomask. The resulting photoresist layer includes unexposed regions, once-exposed regions and twice-exposed regions.

Following the second exposure, the photoresist layer is post-exposure baked and developed using a developer as described above. Unexposed regions corresponding to points of intersection of the lines of the two masks are removed, leaving behind the once- and twice-exposed regions of the resist. The resulting structure can next be patterned as described above with reference to FIG. 1. This method is particularly suited to formation of contact holes in the manufacture of electronic devices.

EXAMPLES

Monomer Synthesis

By the following synthesis method, 1,2:4,5-diisopropylideneribitol can be effectively separated to make pure (isomer free) 1,2:4,5-diisopropylideneribitol-based polymerizable monomers allowing for the preparation of pure bis(2,2-dimethyl-1,3-dioxolan-4-yl)methyl methacrylate monomer.

Synthesis of
bis(2,2-dimethyl-1,3-dioxolan-4-yl)methyl
methacrylate (IPRMA)

Step 1. Synthesis of Diisopropylideneribitol Isomers

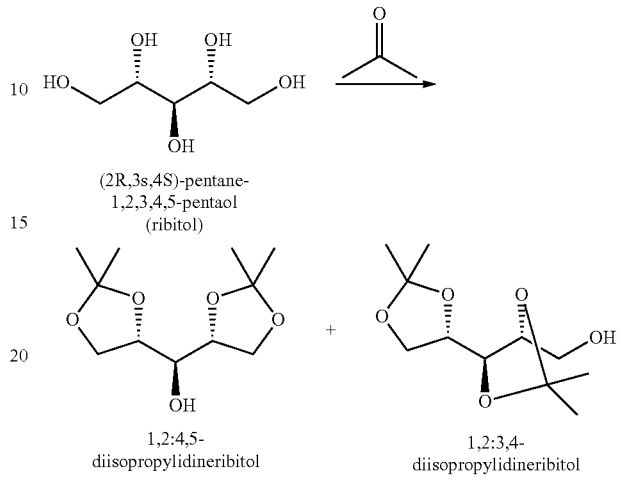

(2R,3s,4S)-pentane-
1,2,3,4,5-pentaol
(ribitol)

1,2:4,5-
diisopropylidineribitol 1,2:3,4-
diisopropylidineribitol

Under nitrogen, zinc chloride (100 g) was dissolved in acetone (900 mL) and the mixture was left under nitrogen overnight. Ribitol (40.00 g, 263 mmol) was added while stirring. The reaction was left stirring at room temperature for 17 h. Approximately 50 g of freshly dried molecular sieve (3 Å) was added and the mixture stirred for another 5 h. The reaction was poured into a solution of 140 g of potassium carbonate in 140 mL of water, covered by 1 L of diethyl ether. The mixture was vigorously stirred using an overhead stirrer for 45 min. The acetone/ether solution was filtered through a Buechner funnel, and the remaining insoluble zinc carbonate residue was washed three times with 100 mL of a 1:1 diethyl ether/acetone mixture. The filtrates were collected and concentrated. The concentrate was diluted with diethyl ether and extracted with brine. The brine solution was extracted once with diethyl ether. The pooled organic phases were dried over anhydrous potassium carbonate. The salt was filtered off and the solvent was removed on the rotary evaporator. The liquid was filtered through a plug of silica (~300 cm$^3$), using several aliquots of diethyl ether. The pooled filtrate was concentrated on the rotary evaporator and dried under high vacuum over night to give 49.7 g of colorless oil as a mixture of 65% (139 mol) of 1,2:4,5-diisopropylidene ribitol (or bis(2,2-dimethyl-1,3-dioxolan-4-yl)methanol) and 29% (62.1 mmol) of 1,2:3, 4-diisopropylidene ribitol and 6% (12.8 mmol) of a third isomer.

Step 2. Separation of Diisopropylideneribitol
Isomers

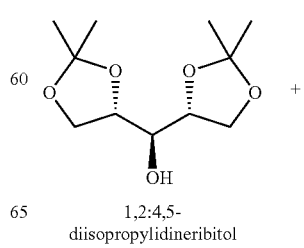

1,2:4,5-
diisopropylidineribitol

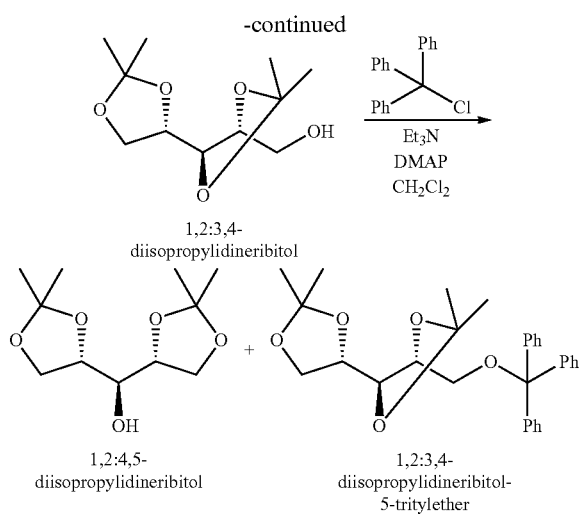

1,2:3,4-diisopropylidineribitol 1,2:4,5-diisopropylidineribitol 1,2:3,4-diisopropylidineribitol-5-tritylether Under nitrogen, 47.0 g of the diisopropylideneribitol isomers (202 mmol, containing ~59.5 mmol of primary alcohol) was dissolved, along with triethyl amine (16.9 mL, 121 mol, 0.6 eq) and DMAP (396 mg, 3.238 mmol, 0.016 eq), in 225 mL dry dichloromethane. Trityl chloride (22.6 g, 80.9 mmol, 0.4 eq) was taken up in a minimal amount of dry dichloromethane and added dropwise to the stirred reaction solution. The mixture was stirred over night at room temperature. The reaction mixture was poured into a saturated solution of sodium bicarbonate and stirred for 30 min. The mixture was extracted three times with diethyl ether. The pooled organic phases were washed once with brine, dried over magnesium sulfate, concentrated on the rotary evaporator and residual volatiles removed under high vacuum. The residue was distilled at 135-140° C., 1.2-1.6 torr, using Kugelrohr distillation to yield 29.3 g of bis(2,2-dimethyl-1,3-dioxolan-4-yl)methanol as a colorless oil.

Step 3. Esterification of bis(2,2-dimethyl-1,3-dioxolan-4-yl)methanol

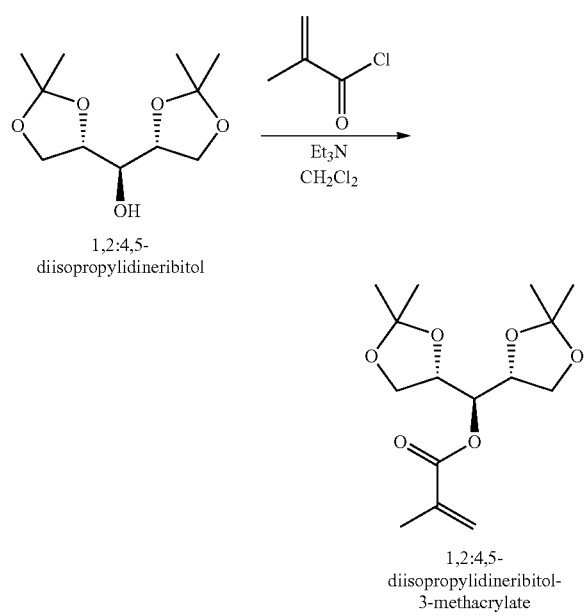

1,2:4,5-diisopropylidineribitol 1,2:4,5-diisopropylidineribitol-3-methacrylate

Under nitrogen, bis(2,2-dimethyl-1,3-dioxolan-4-yl)methanol (29.3 g, 126 mmol, 1.00 eq) was dissolved in dichloromethane (135 mL) along with triethylamine (35.2 mL, 252 mmol 2.0 eq). Methacryloyl chloride (14.8 mL, 15.8 g, 151 mmol, 1.20 eq) in dichloromethane (30 mL) was added dropwise and the mixture was stirred over night. Methanol (5 mL) was added, the reaction stirred for 30 min, and the reaction solution washed several times with diluted brine (⅓ sat.). The aqueous phase was re-extracted once with diethyl ether and the extract pooled with the methylene chloride phase. The organic phase was dried over magnesium sulfate, filtered and concentrated on the rotary evaporator. The concentrate was dissolved in a small amount of diethyl ether, and a white impurity precipitated that was not further characterized. A spatula of magnesium sulfate was added and the solution was filtered through a short plug of celite. The product was completely eluted using several aliquots of diethyl ether, concentrated on a rotary evaporator and dried under high vacuum to 36.0 g of bis(2,2-dimethyl-1,3-dioxolan-4-yemethyl methacrylate (IPRMA) as a colorless oil, which slowly crystallized to a white powder in the freezer.

Matrix Polymer Synthesis

The following monomers were employed in the syntheses of copolymers in the examples below:

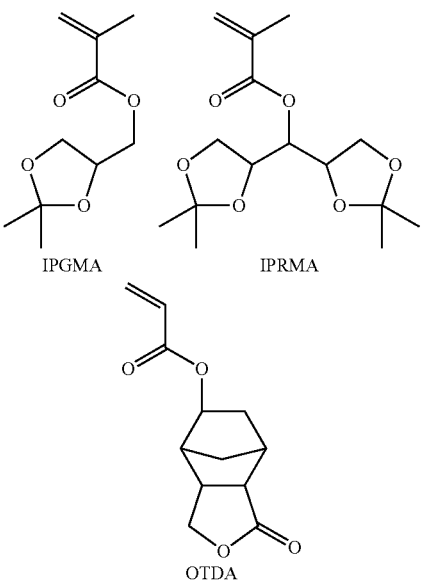

IPGMA                IPRMA

OTDA

Synthesis of poly(IPGMA/OTDA)

Monomers of IPGMA (18.96 g) and OTDA (21.04 g) were dissolved in 60 g of propylene glycol methyl ether acetate (PGMEA). The monomer solution was then degassed by bubbling with nitrogen for 20 min. A 500 mL three-neck flask equipped with a condenser and a mechanical stirrer was charged with PGMEA (32.455 g) and the solvent was degassed by bubbling with nitrogen for 20 min and subsequently brought to a temperature of 80° C. V601 (dimethyl-2,2-azodiisobutyrate) (3.052 g) was dissolved in 8 g of PGMEA and the initiator solution was degassed by bubbling with nitrogen for 20 min. The initiator solution was added into the reaction flask and then monomer solution was fed into the reactor dropwise over the 3 h period under rigorous stirring and nitrogen environment. After monomer feeding was complete, the polymerization mixture was left standing for one additional hour at 80° C. After a total of 4 h of polymerization time (3 h feeding and 1 h post-feeding stirring), the polymerization mixture was allowed to cool down to room temperature. Precipitation was carried out in methyl tert-butyl ether (MTBE) (1671 g). The powder precipitated was filtered, air-dried overnight, re-dissolved in 120 g of THF, and re-precipitated into MTBE (1671 g). The final polymer was collected by filtration, air-dried overnight and further dried under vacuum at 60° C. for 48 h to give 33.5 g (84% yield, Mw=11,117 and Mw/Mn=1.91) of the following "Polymer A":

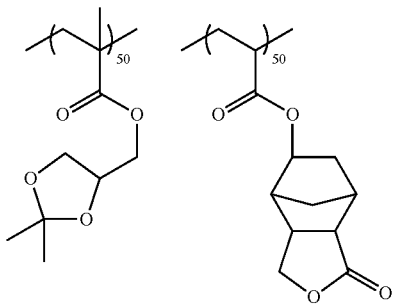

Synthesis of poly(IPRMA/OTDA)

Monomers of IPRMA (14.37 g) and OTDA (10.63 g) were dissolved in 37.5 g of PGMEA. The monomer solution was then degassed by bubbling with nitrogen for 20 min. A 500 mL three-neck flask equipped with a condenser and a mechanical stirrer was charged with PGMEA (18.404 g) and the solvent was degassed by bubbling with nitrogen for 20 min and subsequently brought to a temperature of 80° C. V601 (1.102 g) was dissolved in 8 g of PGMEA and the initiator solution was degassed by bubbling with nitrogen for 20 min. The initiator solution was added into the reaction flask and then monomer solution was fed into the reactor dropwise over the 3 h period under rigorous stirring and nitrogen environment. After monomer feeding was complete, the polymerization mixture was left standing for one additional hour at 80° C. After a total of 4 h of polymerization time (3 h feeding and 1 h post-feeding stirring), the polymerization mixture was allowed to cool down to room temperature. Precipitation was carried out in MTBE (1044 g). The powder precipitated was filtered, air-dried overnight, re-dissolved in 75 g of THF, and re-precipitated into MTBE (1044 g). The final polymer was collected by filtration, air-dried overnight and further dried under vacuum at 60° C. for 48 h to give 17.64 g (70% yield, Mw=10,525 and Mw/Mn=1.63) of the following "Polymer B":

Additive Polymer Synthesis: Poly(n-BMA)

13.01 g of n-butyl methacrylate (nBMA) was dissolved in 7 g of THF. The mixture was degassed by bubbling with nitrogen for 20 min. A 500 mL flask equipped with a condenser, nitrogen inlet and mechanical stirrer was charged with 8 g of THF and the solution brought to a temperature of 67° C. 2.11 g of V601 (10.0 mol % with respect to monomers) was dissolved in 2 g of THF and charged into the flask. The monomer solution was fed into the reactor at a rate of 6.29 mL/h. The monomer feeding was carried out for 3 hours 30 min. After monomer feeding was complete, the polymerization mixture was stirred for an additional 30 min at 67° C. After a total of 4 hours polymerization time (3 hours 30 min feeding and 30 min stirring), 7 g of THF was added to the reactor and the polymerization mixture was cooled down to room temperature. Precipitation was carried out in 0.4 L of cold methanol. After filtration, the polymer was dried in a vacuum oven at 60° C. for 48 hours to give 8.4 g (Mw=12,284 and Mw/Mn=1.79) of the following "Additive A":

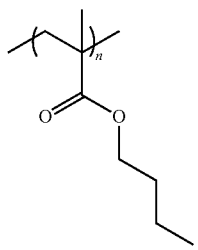

Photoresist Composition Formulation

Example 1 (Comparative)

2.624 g of Polymer A and 0.064 g of Additive A were dissolved in 29.040 g of PGMEA, 19.360 g of cyclohexanone, and 48.400 g of methyl-2-hydroxyisobutyreate. To this mixture were added 0.480 g of "PAG A" described below and 0.032 g of 1-(tert-butoxycarbonyl)-4-hydroxypiperidine. The resulting mixture was rolled on a roller for six hours and then filtered through a Teflon filter having a 0.2 micron pore size.

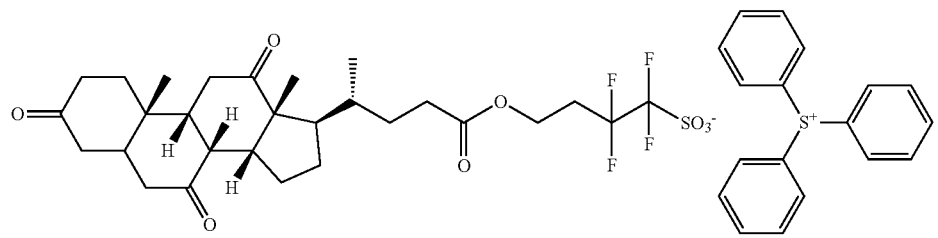

PAG A

Example 2

2.624 g of Polymer B and 0.064 g of Additive A were dissolved in 29.040 g of PGMEA, 19.360 g of cyclohexanone, and 48.400 g of methyl-2-hydroxyisobutyrate. To this mixture were added 0.480 g of PAG A and 0.032 g of 1-(tert-butoxycarbonyl)-4-hydroxypiperidine. The resulting mixture was rolled on a roller for six hours and then filtered through a Teflon filter having a 0.2 micron pore size.

Example 3 (Comparative)

2.784 g of Polymer A and 0.064 g of Additive A were dissolved in 29.040 g of PGMEA, 19.360 g of cyclohexanone, and 48.400 g of methyl-2-hydroxyisobutyrate. To this mixture were added 0.320 g of PAG A and 0.032 g of 1-(tert-butoxycarbonyl)-4-hydroxypiperidine. The resulting mixture was rolled on a roller for six hours and then filtered through a Teflon filter having a 0.2 micron pore size.

Example 4

2.784 g of Polymer B and 0.064 g of Additive A were dissolved in 29.040 g of PGMEA, 19.360 g of cyclohexanone, and 48.400 g of methyl-2-hydroxyisobutyrate. To this mixture were added 0.320 g of PAG A and 0.032 g of 1-(tert-butoxycarbonyl)-4-hydroxypiperidine. The resulting mixture was rolled on a roller for six hours and then filtered through a Teflon filter having a 0.2 micron pore size.

Dry Lithographic Process and Contrast Evaluation

Examples 5-8

Dry lithographic processing was carried out to obtain NTD contrast curves for each of the photoresist compositions of Examples 1-4 on 200 mm silicon wafers using a TEL CleanTrack ACT 8 linked to an ASML/1100 scanner with a maximum numerical aperture (NA) of 0.75. Silicon wafers were spin-coated with AR™77 bottom-antireflective coating (BARC) material (Rohm and Haas Electronic Materials) and baked for 60 seconds at 205° C. to yield a film thickness of 840 Å. Photoresist compositions of Examples 1-4 were coated on the BARC-coated wafers and soft-baked at 90° C. for 60 seconds on a TEL CleanTrack ACT 8 coater/developer to provide a resist layer thickness of 900 Å.

The photoresist-coated wafers were then exposed through a blank mask using 0.75 NA and a Quadrapole 30 illumination condition with 0.89 outer sigma and 0.64 inner sigma. The exposure was carried out with a starting dose of 1.0 mJ/cm² in increments of 0.4 mJ/cm² to expose 100 dies in a 10×10 array on the wafer to cover a dose range from 1.0 to 40.6 mJ/cm². The exposed wafers were post-exposure baked at a temperature of 90 and 85° C. for 60 seconds and then developed using 2-heptanone for 25 seconds on a TEL CleanTrack ACT 8 coater/developer. The remaining film thickness for different exposure doses was measured on a ThermaWave Optiprobe (KLA-Tencor) and NTD contrast curves were obtained by plotting remaining film thickness as a function of exposure energy. From the contrast curves, the threshold energy ($E_{th}$) was determined as the minimum energy to reach constant film thickness and used as a measure of photo-sensitivity of each resist composition for NTD process. A summary of lithographic Examples 5-8 is listed in Table 1.

Figure 2:
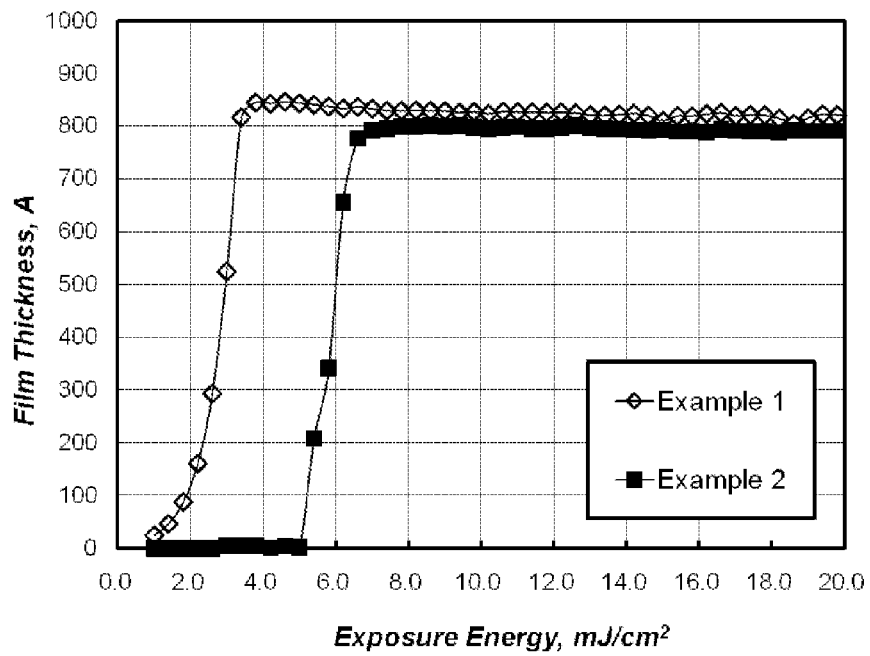
FIGS. 2-3 are contrast curves for photoresist compositions described in the examples.

FIG. 2 compares contrast curves obtained from lithographic Examples 5 and 6 where resist formulation Examples 1 and 2 are compared to see the difference between two leaving group monomers such as IPGMA and IPRMA. IPGMA containing formulation (Example 1) turned to partially insoluble even with the starting exposure energy of 1 mJ/cm² with the current copolymer composition of Polymer A, which limits its process window, and reached its $E_{th}$ value at 3.8 mJ/cm². In contrast, IPRMA containing formulation (Example 2) was completely soluble until the exposure energy reached ~5 mJ/cm² and exhibited its $E_{th}$ value at 7.4 mJ/cm². In order to slow-down the photospeeds with Polymer A and B, lower PAG loading was employed in the formulation Examples 3 and 4 and lower PEB temperature was employed for lithographic Examples 7 and 8.

Figure 3:
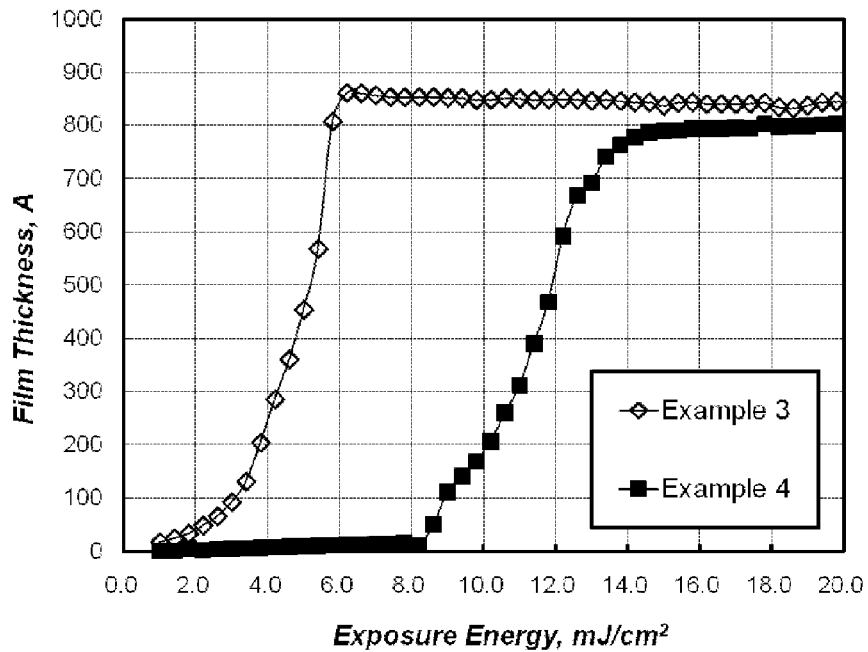

FIG. 3 compares contrast curves obtained from lithographic Examples 7 and 8. Again, the IPGMA containing formulation (Example 3) turned to partially insoluble even with the starting exposure energy of 1 mJ/cm², which limits its process window, and reached its $E_{th}$ value at 6.2 mJ/cm². IPRMA formulation (Example 4) exhibited no photolithographic responses under 8.4 mJ/cm² and then exhibited its $E_{th}$ value at 16.2 mJ/cm². With a given copolymer composition (50/50 copolymer composition with OTDA monomer), it appears that IPRMA exhibits a better process windows in two different formulations (Examples 1-4) and under two different process conditions (Examples 5-8).

TABLE 1

| Ex. | Resist Composition | Matrix Polymer | PAG Loading* | PEB Temp. | $E_{th}$ |
|---|---|---|---|---|---|
| 5(Comp) | Ex. 1 (Comp) | A | 15 wt % | 90° C. | 3.8 mJ/cm² |
| 6 | Ex. 2 | B | 15 wt % | 90° C. | 7.4 mJ/cm² |
| 7 (Comp) | Ex. 3 (Comp) | A | 10 wt % | 85° C. | 6.2 mJ/cm² |
| 8 | Ex. 4 | B | 10 wt % | 85° C. | 16.2 mJ/cm² |

*Based on the weight % of solid excluding solvents

Immersion Lithographic Process

Examples 9-10

300 mm silicon wafers were spin-coated with AR™40A antireflectant (Rohm and Haas Electronic Materials) to form a first bottom antireflective coating (BARC) on a TEL CLEAN TRAC LITHIUS i+ coater/developer. The wafer was baked for 60 seconds at 215° C., yielding a first BARC film thickness of 840 Å. A second BARC layer was next coated over the first BARC using AR™124 antireflectant (Rohm and Haas Electronic Materials), and was baked at 205° C. for 60 seconds to generate a 200 Å top BARC layer. Photoresist formulations of Examples 4-6 were then coated on the dual BARC-coated wafers and soft-baked at 90° C. for 60 seconds on a TEL CLEAN TRACK LITHIUS i+ coater/developer to provide a resist layer thickness of 900 Å.

The photoresist-coated wafers were exposed through a mask on an ASML TWINSCAN XT:1900i immersion scanner using crossed sectoral quadruple (C-Quad) illumination with 1.35 NA, 0.9 outer sigma, 0.7 inner sigma and XY polarization. The exposed wafers were post-exposure baked at 85° C. for 60 seconds and then developed using 2-heptanone for 25 seconds on a TEL CLEAN TRACK™ LITHIUS™ i+ coater/developer to give negative tone patterns. Critical dimensions (CDs) were measured on a Hitachi CG4000 CD SEM using a mask CD at 60 nm (the diameter of an opaque circle on the mask) and a pitch CD at 90 nm (a mask CD plus the distance between opaque circles) to compare the resolution capability of each formulation for ~45 nm contact holes.

Immersion lithographic results are summarized in Table 2. As expected from the NTD contrast curve data under dry lithographic conditions, the IPGMA containing formulation (Example 3) exhibited a much faster photospeed than IPRMA containing formulation (Example 4). Under the same process conditions, IPRMA containing formulation (Example 4)

exhibited better exposure latitude than the comparative IPGMA containing formulation (Example 3).

TABLE 2

| Ex. | Resist Composition | PEB Temp. | $E_s$* | Exposure Latitude |
|---|---|---|---|---|
| 9(Comp) | Ex. 3 (Comp) | 85° C. | 26.7 mJ/cm$^2$ | 1.5 nm/(mJ/cm$^2$) |
| 10 | Ex. 4 | 85° C. | 82.1 mJ/cm$^2$ | 0.6 nm/(mJ/cm$^2$) |

*Exposure energy to print 45 nm holes at 90 nm pitch

What is claimed is:

1. A polymer, comprising:
a first unit formed from a monomer of the following general formula (I):

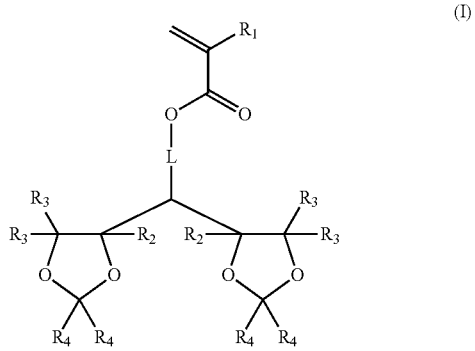

wherein: L represents a single bond or a $C_1$ to $C_{10}$ organic group; $R_1$ represents hydrogen or a $C_1$ to $C_3$ alkyl group; $R_2$ each independently represents a hydrogen atom or a $C_1$ to $C_{10}$ organic group; $R_3$ each independently represents a hydrogen atom or a $C_1$ to $C_{10}$ organic group, those bonded to a common carbon atom together optionally forming a ring; and $R_4$ each independently represents a $C_1$ to $C_{to}$ organic group, those bonded to a common carbon atom together optionally forming a ring; and a second unit comprising a lactone moiety.

2. A photoresist composition, comprising:
a polymer, comprising:
a unit formed from a monomer of the following general formula (I):

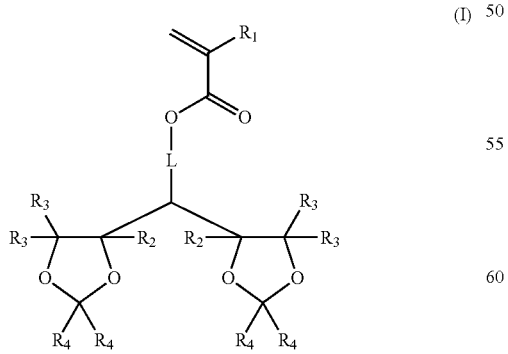

wherein: L represents a single bond or a $C_1$ to $C_{10}$ organic group; $R_1$ represents hydrogen or a $C_1$ to $C_3$ alkyl group; $R_2$ each independently represents a hydrogen atom or a $C_1$ to $C_{10}$ organic group; $R_3$ each independently represents a hydrogen atom or a $C_1$ to $C_{10}$ organic group, those bonded to a common carbon atom together optionally forming a ring; and $R_4$ each independently represents a $C_1$ to $C_{10}$ organic group, those bonded to a common carbon atom together optionally forming a ring; and
a photoacid generator.

3. The photoresist composition of claim 2, wherein the polymer further comprises a second unit comprising a lactone moiety.

4. The photoresist composition of claim 3, wherein the polymer further comprises a third unit comprising an ether, an ester, a polar group or an acid labile moiety, wherein the third unit is different from the first unit and the second unit.

5. The photoresist composition of claim 2, wherein the polymer further comprises a second unit formed from a monomer which is an acid-labile alkyl or alkyloxy (meth)acrylate.

6. A coated substrate, comprising a substrate and a layer of a photoresist composition over a surface of the substrate;
wherein the photoresist composition comprises:
a polymer, comprising:
a unit formed from a monomer of the following general formula (I):

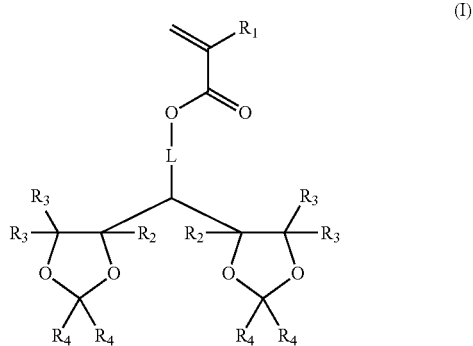

wherein: L represents a single bond or a $C_1$ to $C_{10}$ organic group; $R_1$ represents hydrogen or a $C_1$ to $C_3$ alkyl group; $R_2$ each independently represents a hydrogen atom or a $C_1$ to $C_{10}$ organic group; $R_3$ each independently represents a hydrogen atom or a $C_1$ to $C_{10}$ organic group, those bonded to a common carbon atom together optionally forming a ring; and $R_4$ each independently represents a $C_1$ to $C_{10}$ organic group, those bonded to a common carbon atom together optionally forming a ring; and
a photoacid generator.

7. A method of forming a photolithographic pattern, comprising:
(a) providing a substrate comprising one or more layer to be patterned over a surface of the substrate;
(b) applying a layer of a photoresist composition of over the one or more layer to be patterned;
(c) patternwise exposing the photoresist composition layer to actinic radiation;
(d) heating the exposed photoresist composition layer in a post-exposure bake process; and
(e) applying a developer to the photoresist composition layer to remove a portion of the photoresist layer, thereby forming a photoresist pattern;

wherein the photoresist composition comprises:
a polymer, comprising:
a unit formed from a monomer of the following general formula (I):

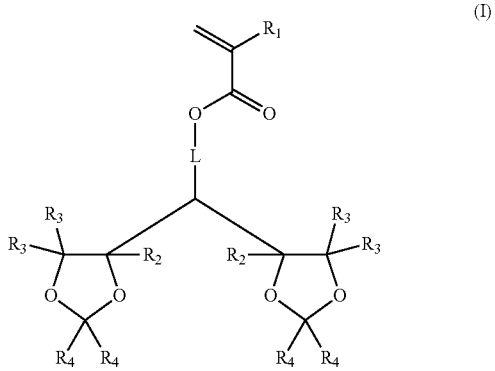

wherein: L represents a single bond or a $C_1$ to $C_{10}$ organic group; $R_1$ represents hydrogen or a $C_1$ to $C_3$ alkyl group; $R_2$ each independently represents a hydrogen atom or a $C_1$ to $C_{10}$ organic group; $R_3$ each independently represents a hydrogen atom or a $C_1$ to $C_{10}$ organic group, those bonded to a common carbon atom together optionally forming a ring; and $R_4$ each independently represents a $C_1$ to $C_{10}$ organic group, those bonded to a common carbon atom together optionally forming a ring; and
a photoacid generator.

8. The method of claim 7, wherein unexposed regions of the photoresist layer are removed by the developer to form the photoresist pattern.

9. The method of claim 8, wherein the developer is 2-heptanone.

10. The method of claim 8, wherein the polymer further comprises a second unit formed from a monomer which is an acid-labile alkyl or alkyloxy (meth)acrylate.

11. The method of claim 8, wherein the polymer further comprises a second unit comprising a lactone moiety.

12. The method of claim 11, wherein the polymer further comprises a third unit comprising an ether, wherein the third unit is different from the first unit and the second unit.

13. The method of claim 11, wherein the polymer further comprises a third unit comprising an ester, wherein the third unit is different from the first unit and the second unit.

14. The method of claim 11, wherein the polymer further comprises a third unit comprising a polar group, wherein the third unit is different from the first unit and the second unit.

15. The method of claim 11, wherein the polymer further comprises a third unit comprising an acid labile moiety, wherein the third unit is different from the first unit and the second unit.

16. The photoresist composition of claim 4, wherein the third unit comprises an ether, wherein the third unit is different from the first unit and the second unit.

17. The photoresist composition of claim 4, wherein the third unit comprises an ester, wherein the third unit is different from the first unit and the second unit.

18. The photoresist composition of claim 4, wherein the third unit comprises a polar group, wherein the third unit is different from the first unit and the second unit.

19. The photoresist composition of claim 4, wherein the third unit comprises an acid labile moiety, wherein the third unit is different from the first unit and the second unit.

20. The coated substrate of claim 6, wherein the polymer further comprises a second unit comprising a lactone moiety.

* * * * *